(12) United States Patent
Wieland

(10) Patent No.: US 8,728,134 B2
(45) Date of Patent: May 20, 2014

(54) IMPLANTATION PIN, FIXATION DEVICE AND METHOD FOR IMPLANTING THE IMPLANTATION PIN

(71) Applicant: Stryker Trauma GmbH, Schönkirchen (DE)

(72) Inventor: Manfred Wieland, Kiel (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 13/904,648

(22) Filed: May 29, 2013

(65) Prior Publication Data
US 2013/0261678 A1 Oct. 3, 2013

Related U.S. Application Data

(63) Continuation of application No. 11/788,761, filed on Apr. 20, 2007.

(51) Int. Cl.
*A61B 17/58* (2006.01)

(52) U.S. Cl.
USPC ........................................ 606/329

(58) Field of Classification Search
USPC .............................. 606/92–95, 151, 300–331
See application file for complete search history.

(56) References Cited

U.S. PATENT DOCUMENTS

| | | |
|---|---|---|
| 5,360,302 A | 11/1994 | MacMartin |
| 5,666,779 A | 9/1997 | Fuchs et al. |
| 5,871,484 A | 2/1999 | Spievack et al. |
| 5,993,458 A | 11/1999 | Vaitekunas et al. |
| 6,080,161 A | 6/2000 | Eaves, III et al. |
| 6,132,214 A | 10/2000 | Suhonen et al. |
| 6,214,012 B1 | 4/2001 | Karpman et al. |
| 6,332,885 B1 | 12/2001 | Martella |
| 6,565,572 B2 | 5/2003 | Chappius |
| 6,623,487 B1 * | 9/2003 | Goshert ..................... 606/329 |
| 6,918,766 B1 | 7/2005 | Hall et al. |
| 7,008,226 B2 | 3/2006 | Mayer et al. |
| 7,250,055 B1 | 7/2007 | Vanderwalle |

(Continued)

FOREIGN PATENT DOCUMENTS

| | | |
|---|---|---|
| JP | 2007222752 A | 9/2007 |
| WO | 2008/034276 A2 | 3/2008 |
| WO | 2008/116203 A2 | 9/2008 |

OTHER PUBLICATIONS

International Search Report, PCT/EP2009/055029, dated Sep. 10, 2009.

*Primary Examiner* — Christopher Beccia
(74) *Attorney, Agent, or Firm* — Lerner, David, Littenberg, Krumholz & Mentlik, LLP

(57) ABSTRACT

An implantation pin for implantation in a target structure has a pinhead and a shaft. The pinhead comprises a pinhead moulding portion comprising a moldable material which can be liquefied by application of mechanical energy such as ultrasonic vibration energy. A channel extends through the pinhead and the shaft, the channel connecting the pinhead molding portion to a discharge opening located at the shaft. The moldable material can be liquefied by applying mechanical energy in the form of ultrasonic vibrations via a fixation device including an ultrasonic sonotrode and a vibrating tip. The pressure applied by the vibrating tip can be transmitted via the border of the pinhead to the target structure while the liquefied mouldable material can be forced through the channel and the discharge opening into a gap between the implantation pin and a recess in a target structure thereby fixing the implantation pin in the target structure.

9 Claims, 3 Drawing Sheets

(56) References Cited

U.S. PATENT DOCUMENTS

| | | |
|---|---|---|
| 7,255,713 B2 | 8/2007 | Malek |
| 7,335,205 B2 | 2/2008 | Aeschlimann et al. |
| 7,354,442 B2 | 4/2008 | Sasso et al. |
| 7,510,397 B2 | 3/2009 | Hochman |
| 7,608,062 B2 | 10/2009 | Sweeney |
| 7,615,070 B2 | 11/2009 | Biscup |
| 7,717,947 B1 | 5/2010 | Wilberg et al. |
| 2003/0003128 A1 | 1/2003 | Chiarelli |
| 2004/0030341 A1* | 2/2004 | Aeschlimann et al. ......... 606/72 |
| 2004/0038180 A1 | 2/2004 | Mayer et al. |
| 2004/0053196 A1 | 3/2004 | Mayer et al. |
| 2005/0059972 A1 | 3/2005 | Biscup |
| 2006/0105295 A1 | 5/2006 | Mayer et al. |
| 2007/0260250 A1 | 11/2007 | Wisnewski et al. |
| 2007/0265704 A1 | 11/2007 | Mayer et al. |
| 2008/0021474 A1 | 1/2008 | Bonutti et al. |
| 2008/0109008 A1 | 5/2008 | Schwager et al. |
| 2008/0125815 A1 | 5/2008 | Heaven et al. |
| 2008/0262517 A1 | 10/2008 | Wieland |

\* cited by examiner

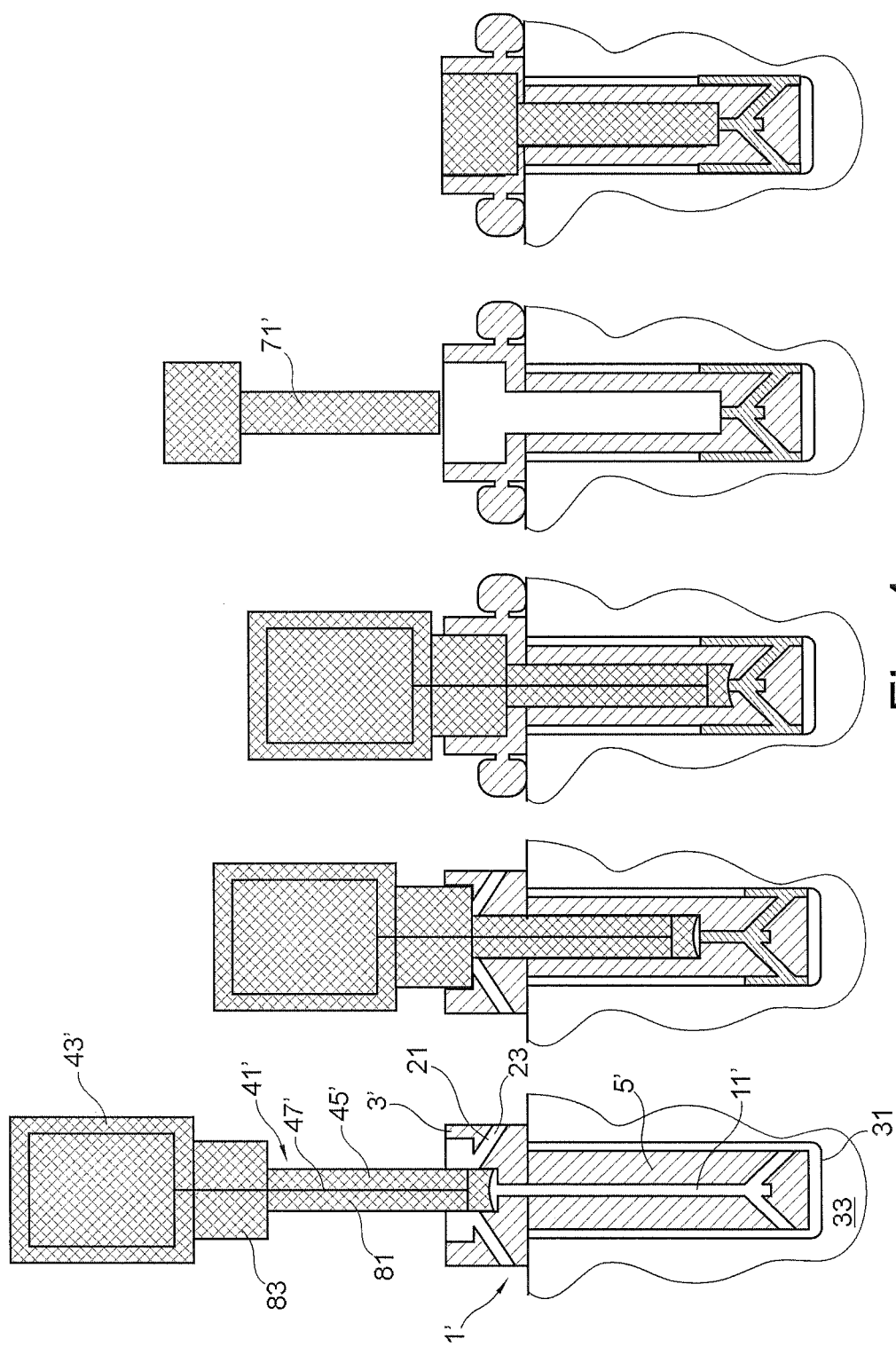

IMPLANTATION PIN, FIXATION DEVICE AND METHOD FOR IMPLANTING THE IMPLANTATION PIN

CROSS-REFERENCE TO RELATED APPLICATION

The present application is a continuation of U.S. patent application Ser. No. 11/788,761, filed on Apr. 20, 2007, the disclosure of which is incorporated herein by reference.

BACKGROUND OF THE INVENTION

The invention relates to an implantation pin, a fixation device, an implantation kit and a method for applying an implantation pin to a target structure. In particular, the invention relates to a bone pin which is formed as a sonic pin.

In the prior art several implantation devices for humans or animals are known. The implants at least partly create positive-fit connections to human or animal tissue parts, particularly skeletal parts, wherein the implants help connect tissue parts together, or help connect tissue parts to means supporting or replacing tissue parts, or to other therapeutic auxiliary devices. Further methods for implanting implants into humans or animals are known.

Known implants for creating connections to skeletal parts such as bones include screws, pins, staples, etc., which are used for connecting bones to bones, or bones to artificial, carrying, stabilizing, or supporting parts, or to parts replacing skeletal parts (stabilization or fixation plates, sutures, wires, artificial joint elements, artificial teeth, bone grafts, etc.). Such connection elements for implantation consist for example of metal or plastic, including resorbable plastic. After healing, the connection elements may be removed by a further operation or they may be left in the body where they are possibly gradually decomposed and replaced by vital tissue.

For stabilizing a bone fracture, a fixation plate with suitable holes may be fixed in the region of the fracture using screws as mentioned above. Plate and screws may consist of metal (e.g. stainless steel or titanium). The screws may be self-cutting and are rotated into threadless openings in the bone, or they may be screwed into pre-drilled threaded openings. Pins may be pushed into previously created openings for similar purposes. Connections created in the foregoing manner are usually based on frictional engagement, possibly on positive fit. Substantial pressure may be applied to living tissue during the implantation.

It is known also to use curable, plastic materials (e.g. particular cements on a water or polymer base) for creating connections of the mentioned type. Such materials are pressed from the outside between implant and vital tissue, or into tissue defects in a highly viscous condition, and are cured in situ. Positive-fit connections can be created using such material, if the openings into which the material is pressed comprise suitable undercuts. In order to reduce the stress and/or costs of the corresponding operation method so-called biodegradable implants, e.g. bone pins, may be used. That is, bone pins which degrade over time and which are then absorbed by the body. One of such known biodegradable bone pins is known under the trademark Polypin. This bone pin consists of a polyactid-copolymer mixture and is absorbed during a period of about two years.

Also known in the art is the usage of thermoplastic polymer materials which can be liquefied in a targeted manner by way of mechanical oscillation such as ultrasonic oscillations and, in this condition, can be pressed into cavities by way of hydrostatic pressure, thereby creating positive fit connections after solidification.

Such implants may serve for creating positive-fit connections to tissue parts and may consist at least partly of a material that can be liquefied at a relatively low temperature (<250° C.) by way of mechanical oscillation energy such that the material can be pressed into pores or other openings of the tissue part by the effect of external pressure to form positive-fit connections when re-solidified.

In a prior art approach an implantation pin for implantation in a target structure comprises a base region and a shaft region. The base region comprises a connection portion which is adapted to interact with a coupling region of a sonotrode applying ultrasonic vibrations. The shaft region comprises a material which can be liquefied by applying ultrasonic vibrations. Accordingly, when ultrasonic vibrations are generated within the sonotrode and transmitted to the base region of the implantation pin, these ultrasonic vibrations are further transmitted to the shaft region. At a surface, where the shaft region abuts to the target structure, such as for example a bone into which a recess has been formed in order to accommodate the implantation pin, the local surface temperature increases due to friction between the target structure and the vibrated implantation pin. This surface temperature increase causes a melting of the liquefiable material such that the latter can then flow into pores of the bone. After re-solidifying of the liquefiable material a positive-fit connection between the implantation pin and the bone may be created.

However, with this prior art implantation pin, the surfaces of the shaft region of the implantation pin which are to be connected to the target structure have to be in direct contact to the target structure while applying the ultrasonic vibrations. For example, when the implantation pin is to be fixed within a bone, it has to be inserted into a previously prepared recess within the bone and has to contact the inside surface walls of the recess in order to liquefy the shaft region material at these locations. For this purpose, it might be necessary to precisely adapt the geometry of the implantation pin to the geometry of the recess in the bone. Furthermore, it might be necessary to exert substantial pressure to the implantation pin while applying the ultrasonic vibrations in order to liquefy the shaft region material and this substantial pressure might be transmitted to the inside surface of the recess at which location the bone might be sensible for damages.

Furthermore, the above prior art implantation pin must have sufficient rigidity in order to transmit the ultrasonic vibrations applied to the base region to the shaft region such that the shaft region is sufficiently vibrated in order to melt the liquefiable material at this shaft location.

Ultrasonic bone implants are disclosed in U.S. Pat. No. 6,921,264 and U.S. Publication No. 2006/0105295 the disclosures of which are incorporated herein by reference.

BRIEF SUMMARY OF THE INVENTION

There may be a need to provide an implantation pin, a fixation device, an implantation kit and a method for applying an implantation pin to a target structure which may overcome the above described deficiencies of the prior art at least in part. Particularly, there may be a need to provide an implantation pin which is adapted such that liquefied moldable material can be provided to an inside of a target structure without applying excessive mechanical stress to the target structure's inside.

This need may be met by an implantation pin, a fixation device, an implantation kit and an implantation method according to the independent claims. Embodiments of the invention are described in the dependent claims.

According to a first aspect of the present invention, an implantation pin for implantation in a target structure is provided wherein the implantation pin comprises a pinhead and a shaft. The pinhead comprises a pinhead moulding portion comprising a moldable material which can be liquefied by application of energy, preferably mechanical energy. In the implantation pin a channel extends along the pinhead and the shaft, the channel connecting the pinhead molding portion to a discharge opening located at the shaft.

The implantation pin according to the invention can be used for implantation in any desired target structure. However, the implantation pin may be specially adapted as a bone pin to be introduced and fixed in bones of humans or animals. For the purpose of implantation, a recess or hole may be prepared in the bone. The recess or hole has a certain geometry with a given cross-section and depth. The implantation pin may then be selected such that its shaft has a corresponding geometry with a slightly smaller cross-section and depth. Accordingly, the implantation pin can be inserted with its shaft into the recess or hole but does not need to have a tight press-fit within the hole.

It may be seen as an aspect of the present invention that the pinhead of the implantation pin is adapted such that, when the implantation pin is inserted in the recess or hole within the target structure, a lower surface of the pinhead being directed substantially in the direction of the shaft may abut on the surface of the target structure surrounding the recess or hole. In such arrangement, an energy source such as an ultrasonic vibration source e.g. in the form of an ultrasonic sonotrode may be applied to the pinhead molding portion such that the moldable material comprised therein may be liquefied by application of mechanical energy in the form of ultrasonic vibrations. The liquefied moldable material can then flow through the channel extending through the pinhead and the shaft to the opposite discharge opening of this channel which is located at a surface of the shaft, the shaft itself being located within the recess or hole. At this location, the liquefied moldable material can fill a remaining gap between the shaft of the implantation pin and the surrounding target structure thereby allowing an advantageous positive fit of the implantation pin in the target structure after re-solidification of the moldable material.

For liquefying the moldable material in the pinhead, the ultrasonic vibration source has to be pressed onto the pinhead in order to efficiently transmit the ultrasonic vibration energy into the pinhead molding portion. However, this pressure is mainly not applied to the possibly sensitive inside surface of the recess or hole within the bone as the shaft does not need to be press-fitted into this recess or hole. Instead, the pressure may be mainly applied to the outer surface of the bone surrounding the recess or hole which is not as sensitive as it has not been damaged previously.

In the following, further features, embodiments and advantages of the present invention are presented.

The pinhead may have any desired geometry and may be adapted to cooperate with a source of mechanical energy such as a source of ultrasonic vibrations. The geometry of the shaft should be adapted to the geometry of the recess in the target structure in which the implantation pin shall be implanted. As the recess is usually prepared by drilling, the shaft may have an elongated geometry with a circular cross-section. As the recess being prepared by a drilling tool may have a conical end portion, the extremity of the shaft distal to the pinhead may also have a corresponding conical shape e.g. in the form of a pointed tip. However, as, in contrast to the prior art implantation pins, the distal extremity of the shaft is not used to apply a high pressure onto the bone while inserting and fixing the implantation pin within the bone, the implantation pin according to the invention does not necessarily need such pointed tip but can also be blunt or flat.

The pinhead molding portion can be a partial portion of the pinhead consisting of a moldable material. Alternatively, the entire pinhead may be made from a moldable material wherein only a partial region of the pinhead will actually be liquefied as the contact surface between the source of mechanical energy and the pinhead is only a part surface of the entire pinhead.

The moldable material can be any material which can be liquefied by application of energy, particularly mechanical energy and more particularly by application of ultrasonic vibration energy. In other words, the moldable material should be such that it is originally solid and becomes liquid or plasticized upon application of energy. Preferably, the moldable material may be adapted in such a way that its liquefaction may be achievable by an energy input which does not destroy or harm human tissue, particularly bone tissue. The moldable material can be for example a thermoplastic material. Such material can liquefy or plasticize at elevated temperatures. For example, the material and the geometry of the implantation pin may be chosen such as to exhibit a sufficient degree of liquefaction at temperatures below a predetermined temperature threshold such as not to substantially harm any tissue. Examples of moldable materials may be thermoplastics such as e.g. PA (Polyamide), PC (Polycarbonate), PP (Polypropylene), PE (Polyethylene), PMMA (Polymethylmethacrylate), POM (Polyoxymethylene), PES (Polyethersulfone), PEI (Polyetherimide), PPSU (Polyphenylsulphone), PEEK (Polyetheretherketone), PSU (Polysulfone) or the bio-compatible or bio-resorbable materials mentioned further below.

The liquefaction of the moldable material should be such that the liquefied material can easily flow through the channel extending from the pinhead molding portion. Accordingly, the liquefied material should have such low viscosity that it can be pushed through the channel without applying excessive pressure onto the implantation pin in order not to damage or harm the target bone structure.

One main characteristic feature of the implantation pin according to the invention may be seen in the channel connecting the pinhead molding portion to a discharge opening located spaced apart from this moulding portion. This channel allows a spatial separation between the location of applying the mechanical energy thereby liquefying the moldable material and the location of applying the liquefied material in a region between the implantation pin's shaft and the surrounding target structure. Furthermore, the region where the pressure applied from a mechanical energy source is transmitted onto the target structure such as the bone and the region where the liquefied material is applied to the target structure via the channel can be different.

It is to be noted that a single channel connecting the pinhead molding portion to a single discharge opening at the shaft may be sufficient. However, a plurality of channels and/or a channel branching into plural branches and leading to a plurality of discharge openings located at different positions at the shaft and/or at the pinhead may be provided in order to distribute the liquefied moldable material in an advantageous manner to a plurality of locations within the recess in the target structure in which the implantation pin is to be located.

According to a further embodiment of the present invention the channel extends internally through the pinhead and the shaft. In other words, the channel has its origin adjacent to the pinhead molding portion and then runs down through the shaft to the discharge opening. For example, the channel can extend along a middle longitudinal axis of the implantation pin.

According to a further embodiment of the present invention the at least one discharge opening of the channel is positioned at a lateral surface of the shaft. In this way, the liquefied moldable material can be transferred to the circumferential surface of the shaft such that a positive fit between the lateral surface of the shaft and the side walls of the recess in the target structure can be obtained.

According to a further embodiment of the present invention the discharge opening is located at an extremity of the shaft distal from the pinhead. In other words, at least one discharge opening of the channel may discharge into the recess in the target structure at a position closer to a distal end of the shaft than to the pinhead. Preferably, the discharge opening is located in a direct proximity to the distal end of the shaft. Thereby, liquefied moldable material can exit the channel at a position deep inside the recess within the target structure thereby supporting a secure fixation of the shaft within this recess.

According to a further embodiment the shaft comprises a shaft molding portion adjacent to the channel, the shaft molding portion comprising moldable material which can be liquefied by application of mechanical energy. In other words, the implantation pin comprises both a pinhead molding portion and a shaft molding portion where the material can be liquefied by application of e.g. ultrasonic vibration energy. Accordingly, the molding portions are not only limited to the pinhead but also extend into the shaft thereby providing a larger volume of moldable material. Preferably, the shaft molding portion is located directly adjacent or continuous to the pinhead molding portion. Furthermore, the moldable materials of the pinhead molding portion and the shaft molding portion may be same or similar.

According to a further embodiment the implantation pin consists entirely of one single material. In this embodiment, the entire implantation pin can be made from a moldable material and can be fabricated for example as a single integral component. In this embodiment, the pinhead molding portion and/or the shaft molding portion may be defined as partial areas of the implantation pin which, in use, are actually liquefied by application of mechanical energy e.g. by using an ultrasonic sonotrode the geometry of which is specially adapted to the geometry of the implantation pin. Providing the entire implantation pin with only one material may significantly simplify the fabrication of such pin. For example, the pin may be made by injection molding.

According to a further embodiment of the present invention the pinhead has a larger lateral dimension perpendicular to a longitudinal axis of the pin than the shaft. In other words, with respect to a width perpendicular to the longitudinal axis of the pin the pinhead is wider than the shaft. In this embodiment, if both the pinhead and the shaft have a circular cross-section, the radius of the pinhead is larger than the radius of the shaft. Accordingly, the pin can be introduced with its shaft into a recess in the target structure until the wider pinhead abuts to the circumferential border of the recess. The shaft itself may not or may only slightly contact the surfaces of the recess in the target structure. Thereby, when pressure and vibrations are applied to the implantation pin, forces are mainly transmitted to the outer surface of the target structure such as a bone whereas the inner part of the bone within the recess accommodating the shaft will not or only slightly be loaded.

According to a further embodiment the channel discharges into a plurality of discharge openings at various surface portions, preferably at opposing lateral surface portions, of the shaft. In other words the channel coming from the molding portion may branch off in several sub-channels which may lead to a plurality of discharge openings. These discharge openings may be positioned at the lateral surface of the shaft at opposing locations such that the liquefied moldable material coming from the molding portion can be distributed homogeneously around the lateral surfaces of the shaft. The sub-channel(s) may branch off from the middle main-channel in an obtuse angle in order to improve flowing properties of liquefied moldable material through the channels.

According to a further embodiment, an additional channel extends through the pinhead the channel connecting the pinhead molding portion to a discharge opening located at a surface portion of the pinhead. In other words, one or more additional channels can be provided within the implantation pin such that the pinhead molding portion is not only connected to one or more discharge openings at the shaft but also to one or more additional discharge openings located at the pinhead at a surface which, in use, is directed to or close to the target structure into which the implantation pin is to be implanted. Thereby, additional stability of the connection between the implantation pin and the target structure can be obtained as the implantation pin is not only "glued" to the inside of a recess in the target structure but also the pinhead of the implantation pin is "glued" to the surface of the target structure.

According to a further embodiment, at least one of a surface coating of the implantation pin, a bulk material of the implantation pin and the moldable material comprises a bio-compatible material. A bio-compatible material may be a material which does not negatively interfere with human or animal tissue. Examples of bio-compatible materials may be specially adapted metal alloys such as titanium or specific plastics, e.g. PEEK (Polyetheretherketone), UHMWPE (Ultra high molecular weight polyethylene), PLA (Polylactic acid), PLLA (Poly-L-lactide), PLDLA (Poly(D,L-Lactide)), PDLLA (Poly-DL-lactide), PVDF (Polyvinylidene Difluoride). Such bio-compatible materials may be used especially for the outer "skin" of the implantation pin in order to avoid rejection of the implantation pin when implanting the pin for example into a bone. It is advantageous to use a bio-compatible thermoplastics which can be used both for the outer skin of the pin as well as for the inner moldable material such that the entire implantation pin can be made of this single bio-compatible material.

According to a further embodiment at least one of a surface coating of the implantation pin, a bulk material of the implantation pin and the moldable material comprises a bio-absorbable material. Such bio-absorbable material may be absorbed by a human or animal's body after a certain period such that parts of the pin consisting of such bio-absorbable material may be replaced by living tissue after this period, thereby providing an increased stability of the connection between implantation pin and living tissue and reducing rejection reactions.

One possible bio-absorbable material comprises a copolymer comprising between 50% and 90% Poly-L-lactide and between 10% and 50% Poly-D, L-lactide. In particular, the bio-absorbable material may be a copolymer comprising 70 weight % Poly-L-lactide and 30 weight % Poly-D, L-lactide. Preferably, the bio-absorbable material may be formed as an amorphous material.

The above described material may be a suitable material for an implantation pin, which material may exhibit a suitable tensile strength of about 60 MPa, and a suitable E-modulus of about 3500 MPa. Furthermore, an implantation pin including the above material, may retain its strength for about a sufficient time when implanted into a human or animal's body, such a time span may be about 16 to 26 weeks. The described copolymer may have a resorption time of about two to three years in a human or animal's body. The material may further exhibit an increase of implant volume up to 200% after 24 month from the implantation in the target structure. Such a material may further be easily to be sterilized by γ-radiation. A suitable energy dose may be between 20 kGy and 30 kGy, in particular below 25 kGy.

A further aspect of the present invention is directed to a fixation device which is adapted for fixing an implantation pin according to the above first aspect. The fixation device comprises an ultrasonic sonotrode comprising a vibration shaft adapted to generate ultrasonic vibrations at a tip provided on the vibration shaft. Furthermore, the fixation device comprises a guiding mechanism adapted to cooperate with the implantation pin in order to align the guiding mechanism with respect to the implantation pin and adapted to guide the vibration shaft and/or the tip provided at the shaft.

It may be seen that this aspect of the invention is to provide a fixation device which, on the one hand, includes an ultrasonic vibration source and which, on the other hand, is adapted to apply the generated ultrasonic vibrations in a predetermined way to the above described implantation pin according to the first aspect of the invention in order to liquefy the moldable material of the implantation pin in the region of the moldable portion(s). In order to be able to apply the ultrasonic vibrations in such predetermined manner, the sonotrode comprises a tip at which ultrasonic vibrations are generated. Furthermore, a guiding mechanism is provided such that the position and moving direction of the vibrated tip can be controlled as desired during an operation. Specifically, the guiding mechanism may be adapted such that it may cooperate with structures of the implantation pin such as for example the surface or the circumference of the pinhead in order to align the position of the fixation device with respect to the implantation pin. For this purpose, the guiding mechanism may have specially adapted abutment surfaces in order to hold or fix the guiding mechanism to the implantation pin.

Furthermore, the guiding mechanism may be adapted to guide the vibration shaft and/or the tip relative to the implantation pin. For example, the guiding mechanism may have a sliding mechanism such that, after being fixed relative to the implantation pin, the tip of the ultrasonic sonotrode can be slid or moved in a predetermined direction with respect to the guiding mechanism. In this way, the vibrating tip may be moved further into the molding portion of the implantation pin while liquefying the moldable material therein and thereby pushing the liquefied moldable material through the channel of the implantation pin.

The ultrasonic sonotrode may be adapted to generate ultrasonic vibrations at the tip with a frequency of between 10 and 50 kHz, preferably between 20 and 30 kHz, and a suitable vibration amplitude may be in the range between 1 and 100 µm, preferably between 5 and 30 µm. The vibrations can be generated preferably in a direction along the vibration shaft and/or in a direction perpendicular to the vibration shaft. The entire construction of the sonotrode including the shaft and the tip should be adapted such that the ultrasonic vibrations can be suitably transmitted via the vibration tip to a target region in an implantation pin. For example, the shaft and the tip should comprise sufficient rigidity in order to transmit the vibration energy via the vibration tip.

The guiding mechanism may be suitably adapted to hold or guide the sonotrode and/or its vibrating tip with respect to the implantation pin to which the guiding mechanism is fixed. Furthermore, a damping element may be provided on the guiding mechanism such that vibrations from the sonotrode are not substantially transmitted to the guiding mechanism in order to avoid that the implantation pin is vibrated through the guiding mechanism at undesired locations.

According to a further embodiment, the guiding mechanism is adapted to guide the vibration shaft in a direction parallel along the longitudinal axis of the implantation pin. In other words, the vibrating tip arranged at the vibration shaft can be advanced in a direction parallel to the longitudinal axis of the implantation pin guided by the guiding mechanism which itself may be fixed in relation to the implantation pin. In this way, the fixation device may be used for liquefying the moldable material of the implantation pin in predetermined regions, namely e.g. regions along the longitudinal middle axis of the implantation pin. As the channel of the implantation pin preferably also extends along this middle axis, the vibrating tip which preferably has a larger lateral dimension than the channel of the implantation pin, may be pushed into the moulding portion of the implantation pin while liquefying the moldable material therein and thereby pushing the liquefied moldable material through the channel.

According to a further embodiment the tip on the vibration shaft has a smaller lateral dimension perpendicular to the longitudinal axis of the shaft than the pinhead of the implantation pin. In other words, the width of the tip is smaller than the width of the pinhead or, again in other words, the contact surface between the vibrating tip and the pinhead is smaller than the entire surface of the pinhead. Accordingly, when the vibrating tip is in contact with the pinhead of the implantation pin, only a partial region of the pinhead which may correspond to the pinhead molding portion may be liquefied. Particularly, the geometry and/or cross-section of the vibrating tip may be adapted to correspond to the geometry and/or cross-section of a molding portion of a given implantation pin.

According to a further embodiment the tip on the vibration shaft has a smaller lateral dimension perpendicular to the longitudinal axis of the vibration shaft than the shaft of the implantation pin. In other words, the width or the cross-section of the vibrating tip may be smaller than the width or the cross-section of the shaft of the implantation pin. Accordingly, the vibrating tip can be pushed for example into the shaft molding portion of the shaft of the implantation pin in order to liquefy the moldable material in this part of the pin's shaft.

According to a further embodiment the tip on the vibration shaft may have regions of different lateral dimensions. In other words, the width or the size of the cross-section of a tip may vary along the direction of the longitudinal axis of the vibration shaft. Accordingly, while liquefying the moldable material and pushing the vibrating tip into the implantation pin regions of different cross-section can be liquefied. For example, a distal portion of the vibrating tip may have a smaller width than the shaft of the implantation pin whereas a proximal portion is wider than the distal portion and has a width being slightly smaller than the width of the pinhead of the implantation pin but possibly wider than the shaft of the implantation pin.

According to a further aspect of the invention an implantation kit is provided including an implantation pin according to the first aspect of the invention. Furthermore, the implantation kit may comprise a fixation device according to the second aspect of the invention. Additionally, the implantation kit may comprise further elements or components such as for example a multitude of implantation pins of different geometry such that a surgeon can choose an implantation pin which matches the geometry of a recess previously prepared in a bone. Furthermore, a plurality of vibrating tips for the sonotrode may be included in the implantation kit wherein the tips may have different geometries adapted to different implantation pins.

According to a further aspect of the present invention a method for implanting an implantation pin according to the first aspect is provided. The method comprises: inserting the implantation pin into a target structure; applying ultrasonic vibrations to the pinhead molding portion of the implantation pin thereby liquefying moldable material in the pinhead molding portion; and forcing the liquefied moldable material through the channel of the implantation pin.

For applying the ultrasonic vibrations and/or for pushing the liquefied moldable material into the channel a fixation device according to the above described second aspect of the invention may be used.

According to an embodiment, the method further comprises preparing a recess in the target structure, e.g. a bone, such that the implantation pin can be inserted into the recess such that a main contact between the implantation pin and the target structure appears between the pinhead of the implantation pin and a border region around the recess. In other words, the geometry of the recess and the geometry of the implantation pin to be fixed therein may be adapted such that the implantation pin fits into the recess such that a small gap between the implantation pin and the recess walls remains or such that there is only slight contact between the surface of the shaft of the implantation pin and the walls of the recess. Then, the pinhead preferably having a larger width than the pin's shaft abuts to the surface of the target structure in the border region around the recess thereby preventing further introducing the implantation pin deeper into the recess. When ultrasonic vibrations are applied to the implantation pin the occurring pressure is then mainly transmitted to the surface of the target structure bordering the recess instead of being applied to a surface within the recess.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless otherwise notified, in addition to any combination of features belonging to one type of subject matter also any combination between features relating to different subject matters, in particular between features of the apparatus type claims and features of the method type claims is considered to be disclosed with this application.

The aspects and embodiments defined above and further aspects and embodiments of the present invention are apparent from the examples of embodiments to be described hereinafter and are explained with reference to the examples of embodiment. The invention will be described in more detail hereinafter with reference to examples of embodiment but to which the invention is not limited.

BRIEF DESCRIPTION OF THE DRAWINGS

It is to be noted that the figures are only schematic and not to scale. Corresponding reference signs have been used throughout the figures to designate similar elements.

DETAILED DESCRIPTION

Figure 1:
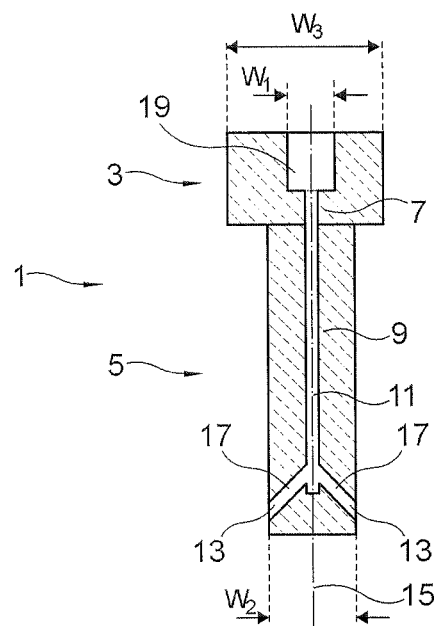
FIG. 1 shows an implantation pin having an inside channel according to an embodiment of the present invention.

FIG. 1 shows an implantation pin 1 including a pinhead and a shaft 5. The entire implantation pin is made as an integral part from a moldable material being bio-compatible or bio-resorbable. The pinhead 3 comprises a pinhead moulding portion 7. The shaft 5 comprises a shaft molding portion 9. Both molding portions 7, 9 are arranged adjacent to a channel 11 which connects the molding portions 7, 9 to discharge openings 13 located at a distal extremity of the shaft 5. The channel 11 is arranged linearly along the longitudinal axis 15 of the implantation pin and two sub-channels 17 connect the channel 15 in the middle of the pin to the lateral surface of the shaft.

The width $w_2$ of the shaft 5 is smaller than the width $w_3$ of the pinhead. At the upper surface of the pinhead 3 a cylindrical recess 19 is provided. The recess 19 has a smaller lateral dimension $w_1$ than the lateral dimension $w_2$ of the shaft 5.

Figure 2:
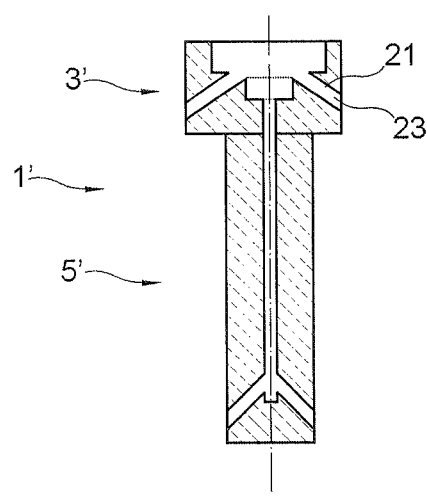
FIG. 2 shows an implantation pin having an additional channel at the pinhead according to a further embodiment of the present invention.

The implantation pin 1' in FIG. 2 further includes additional channels 21 which lead to discharge openings 23 located at a lateral lower surface portion of the pinhead 3'.

Figure 3:
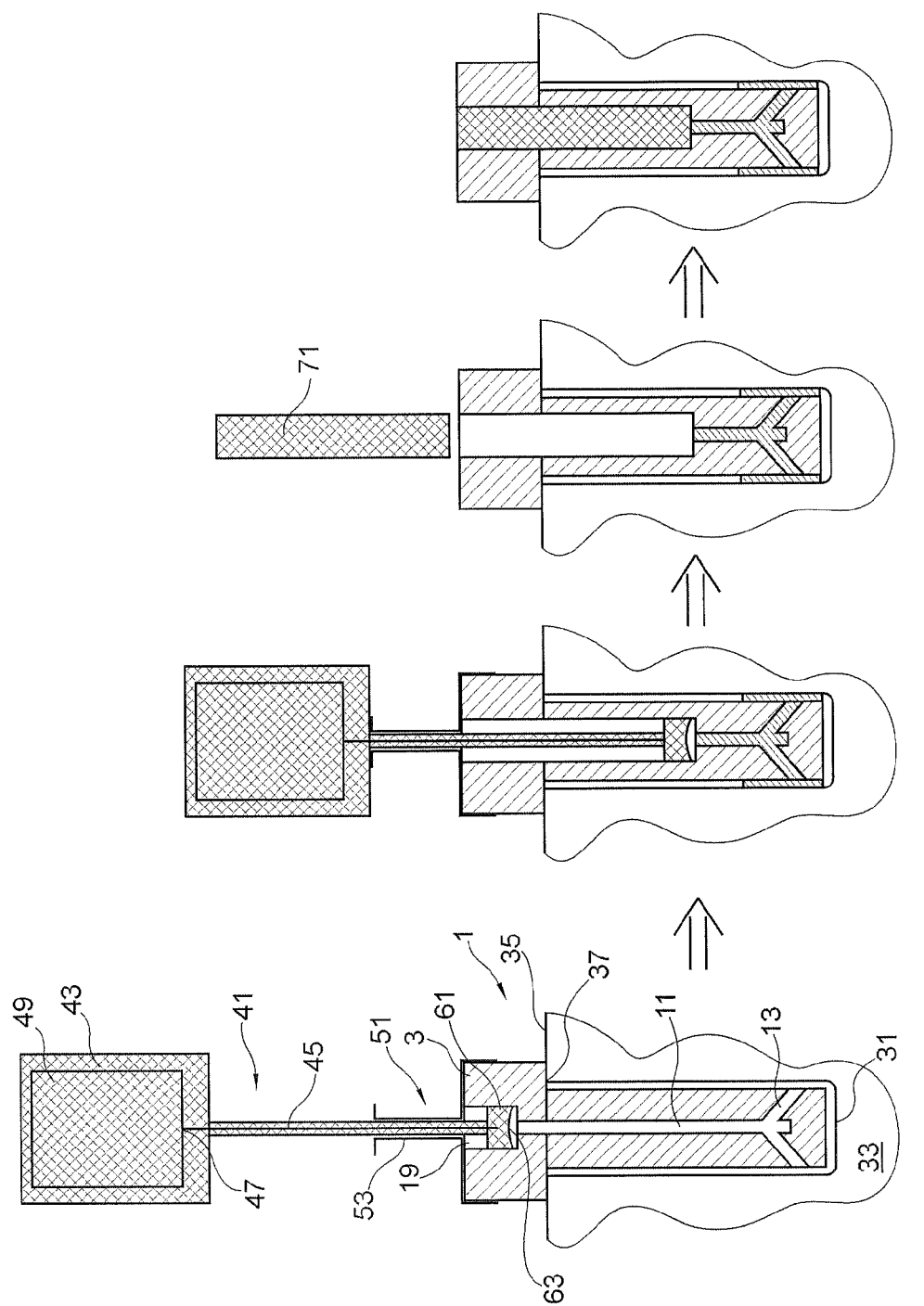
FIG. 3 illustrates an implantation method using an implantation pin and a fixation device according to an embodiment of the present invention; and, FIG. 4 illustrates an implantation method using an implantation pin and a fixation device according to an alternative embodiment of the present invention.

With respect to FIG. 3 an embodiment of a method for implanting and fixing an implantation pin according to an embodiment of the invention is described.

First, a recess 31 is drilled into a target structure 33 such as a bone. Then, an implantation pin 1 as shown in FIG. 1 is inserted into the recess 31. Therein, an implantation pin 1 with such a geometry is chosen such that the outline of the implantation pin 1 is slightly smaller than the recess 31 such that a small gap between the recess 31 and the implantation pin 1 is established. The pinhead 3 of the implantation pin 1 abuts to the upper surface 35 of the bone 33 in a contact region 37.

A fixation device 41 is set on top of the implantation pin 1. The fixation device 41 comprises a sonotrode 43 with a vibration shaft 47 and a tip 45 provided on the vibration shaft 47. The sonotrode 43 includes an ultrasonic vibration generator to which the vibration shaft 47 is fixed. The ultrasonic vibrations generated by an ultrasonic generator 49 are transmitted to the tip 45 via the vibration shaft 47.

In order to align the fixation device 41 with respect to the pin 1 a guiding mechanism 51 is provided. The lower portion of the guiding mechanism 51 is adapted to cooperate with the pinhead 3. In the upper portion of the guiding mechanism 51 there is a sliding mechanism 53 which is adapted such that the shaft 47 of the sonotrode is linearly guided when sliding along the sliding mechanism 53. Furthermore, the recess 19 in the pinhead 3 may help in aligning the tip 45.

The distal part of the vibrating tip 45 comprises a cylindrical end portion 61 having a concave surface 63 on its lower end.

When the tip 45 guided on the vibration shaft 47 is excited with ultrasonic vibrations the mouldable material of the implantation pin 1 liquefies in a contact region between tip's cylindrical end portion 61 and pin 1. As the tip 61 is pushed towards the distal end of the pin 1 the liquefied moldable material is forced through the channel 11 in the pin and exits through the discharge openings 13 into the gap between the pin 1 and the recess 31.

After resolidification of the moldable material the pin is reliably fixed within the recess 31. During the fixation process, no excessive force has been applied to the inside of the recess 31 but the pressure applied by the tip 45 of the sonotrode 41 is mainly transmitted to the contact surface 37 and thereby applied to an outer surface 35 of the bone.

After the fixation device has been withdrawn from the pin 1 a spacer element 71 is used to fill the remaining space within the pin 1 which has been generated when pushing the vibrating tip 61 through the moldable portions of the pin 1. Accordingly, the cross-section of the spacer 71 should substantially correspond to the cross-section of the vibrating tip 61. The spacer element 71 can be of any material as it is not in direct contact with the vital tissue. For example, the spacer element 71 can be provided with a metal such as to stabilize the implantation pin itself consisting of a moldable plastics.

With respect to FIG. 4, an alternative embodiment of a method for implantation and fixing an implantation pin 1' as shown in FIG. 1 is described.

The implantation pin 1' further comprises channels 21 in the pinhead 3'.

The fixation device 41' comprises a sonotrode 43' with a vibration shaft 47' on which a vibrating tip 45' is provided. The tip 45' comprises a lower portion 81 with a width smaller than the width of the shaft 5' of the pin 1. When fixing the pin in the recess 31, first this lower portion 81 of the tip 45' is pushed into the implantation pin 1' by liquefying the moldable material.

The tip 45' further comprises an upper portion 83 having a width wider than the lower portion 81. While pushing the vibrating tip 45' into the pin and thereby pressing the moldable material through the channel 11' and into the gap between the pin 1' and the recess 31, the upper portion 83 will contact the upper surface of the pinhead 3' after a certain distance. The upper portion 83 of the tip 45' will then liquefy additional moldable material in the pinhead 3' and this material will flow through the additional channels 21 and exit from the discharge opening 23 lying above the surface of the bone. The liquefied moldable material will flow to the surface of the bone and "glue" the pinhead 3' to the bone in this region.

Again, after removing the fixation device from the fixed pin, a spacer 71' is introduced in the remaining hollow space within the pin 1'.

It should be noted that the terms "comprising" or "including" do not exclude other elements or steps and the "a" or "an" does not exclude a plurality. Also elements described in association with different embodiments and aspects may be combined. It should also be noted that reference signs in the claims shall not be construed as limiting the scope of the claims.

The invention claimed is:

1. A method for implanting an implantation pin in a target structure comprising providing an implantation pin consisting entirely of a material which can be liquefied by applying ultrasonic vibrations, the implantation pin comprises a pinhead, a shaft comprising a discharge opening wherein a channel extends internally along and through the pinhead and the shaft, the channel connecting the pinhead molding portion to the shaft discharge opening, wherein material of the pinhead molding portion when liquefied by applying ultrasonic vibrations, can be pressed through the channel and out of the discharge opening; inserting the implantation pin into bone and applying ultrasonic vibrations with an ultrasonic sonotrode comprising a vibration shaft adapted to generate ultrasonic vibrations at a tip provided on the vibration shaft wherein the tip on the vibration shaft has a width being smaller than a width of the shaft of the implantation pin and being larger than a width of the channel within the shaft of the implantation pin; and guiding the vibrating tip of the ultrasonic sonotrode with a guiding mechanism adapted to cooperate with the implantation pin in order to align the guiding mechanism with respect to the implantation pin.

2. The method according to claim 1, wherein the guiding mechanism guides the vibration shaft in a direction parallel along the longitudinal axis of the implantation pin.

3. The method according to claim 1 wherein the tip on the vibration shaft has smaller lateral dimension perpendicular to the longitudinal axis of the shaft than the pinhead of the implantation pin.

4. The method according to claim 1 wherein the tip on the vibration shaft has smaller lateral dimension perpendicular to the longitudinal axis of the shaft than the shaft of the implantation pin.

5. A method for implanting an implantation pin in a target structure;

providing an implantation pin comprising a one-piece molded body having first and second ends spaced along an axis, the body having a head portion at the first end and a shaft portion extending from the head portion to the second end of the body, the head portion having an outer surface having a larger dimension in a direction transverse to the axis than the shaft portion, the body comprises a solid material which can be liquefied by the application of ultrasonic energy, the body having an internal axially extending channel therethrough extending from the first to adjacent the second end, the channel having an enlarged area with a larger transverse dimension in the head portion, the enlarged area open to the first end of the body, the enlarged area capable of receiving a tip of a vibrating tool inserted therein through the open first end of the body and the channel in the shaft portion having first and second discharge channels extending radially outwardly from the axially extending channel to an outer surface of the shaft portion adjacent the body second end and the axially extending channel in the head portion having third and fourth discharge channels extending radially outwardly from the axially extending channel to the outer surface of the head portion, the third and fourth discharge channels located above an outer surface of the target structure when the head portion contacts the outer surface of the target structure, inserting the implantation pin into the target structure;

applying ultrasonic vibration to the pin thereby liquefying the solid material; and forcing the liquefied material through the channel of the implantation pin and out the discharge channels.

6. The method as set forth in claim 5 wherein the first and second discharge channels extend on opposite sides of the shaft.

7. The method according to claim 6 wherein the radially extending discharge channels extend at an angle towards the second end of the shaft.

8. The method according to claim 5 wherein the molded body comprises a bioabsorbable polymer that can be liquefied by application of energy in the form of ultrasonic vibrations.

9. The method as set forth in claim 1 wherein the tip of the ultrasonic sonotrode comprises a cylindrical end portion having a concave surface on its distal region.

\* \* \* \* \*